(12) United States Patent
Persinger

(10) Patent No.: US 7,162,976 B2
(45) Date of Patent: Jan. 16, 2007

(54) METHOD FOR REDUCING BACTERIAL CONTAMINATION AND INFECTIOUS DISEASES IN LIVESTOCK AND OTHER ANIMALS

(76) Inventor: James Persinger, 1200 Industrial, Hugoton, KS (US) 67951

( * ) Notice: Subject to any disclaimer, the term of this patent is extended or adjusted under 35 U.S.C. 154(b) by 14 days.

(21) Appl. No.: 10/790,317

(22) Filed: Feb. 28, 2004

(65) Prior Publication Data

US 2004/0200431 A1      Oct. 14, 2004

Related U.S. Application Data

(63) Continuation-in-part of application No. 10/153,162, filed on May 20, 2002, now abandoned.

(51) Int. Cl.
*A01K 1/03*     (2006.01)
(52) U.S. Cl. .................................. 119/420; 55/515
(58) Field of Classification Search ............... 424/438, 424/442, 405, 406, 613; 119/420; 55/515, 55/516, 518
See application file for complete search history.

(56) References Cited

U.S. PATENT DOCUMENTS

| | | | |
|---|---|---|---|
| 3,421,999 A * | 1/1969 | Corwin | 422/186.15 |
| 4,834,836 A * | 5/1989 | Wemhoff | 159/23 |
| 4,932,400 A * | 6/1990 | Persinger | 128/202.25 |
| 5,983,834 A * | 11/1999 | Tai | 119/448 |
| 6,352,076 B1 * | 3/2002 | French | 128/203.12 |
| 6,725,859 B1 * | 4/2004 | Rothenberg et al. | 128/200.23 |

* cited by examiner

*Primary Examiner*—Son T. Nguyen
*Assistant Examiner*—Bethany L Griles
(74) *Attorney, Agent, or Firm*—Frank Frisenda

(57) ABSTRACT

An improved method is provided for treatment of feed water for livestock and other animals to reduce bacterial contamination while at the same time improving live performance. A gaseous mixture comprising ozone and oxygen gas is produced from ambient air and directly contacted with a supply of water to produce a solution of gaseous mixture. This contact step is continued until the content of ozone in the water supply is within a range of from about 5 parts per million to about 20 parts per million, and the content of oxygen is between about 80% and 97% of saturation. Thereafter, the resultant water product is directed for use as feed water to livestock or other animals to be treated.

5 Claims, 1 Drawing Sheet

METHOD FOR REDUCING BACTERIAL CONTAMINATION AND INFECTIOUS DISEASES IN LIVESTOCK AND OTHER ANIMALS

CROSS REFERENCE TO RELATED APPLICATION

This application is a continuation-in-part of my prior U.S. application Ser. No. 10/153,162, filed May 20, 2002 now abandoned.

BACKGROUND OF THE INVENTION

The present invention relates to an improved method for treatment of feed water for livestock and other animals to reduce bacterial contamination while at the same time improving live performance.

Among today's meat producers, it is increasingly important to inhibit diseases caused by bacterial infection. The portal of infection most often is via the animals' mouth into its digestive tract. Thereafter, the harmful bacteria may remain in a carrier state such as feces and spread to an entire common population group. For instance, the harmful bacteria may, in turn, be passed from animal to animal by means of feces contamination in a common water source, common feed source or licking of other animals. Free flying birds may also pose a source of contamination in both water and feed. Accordingly, owing to increased population density of animals, for example, growing pens, the reduction and inhibition of such sources of bacterial contamination is essential.

It is generally known, Colibacillosis occurs in all species of newborn farm animals and is a major cause of losses in this age group. Gut edema, enteric colibacillosis of feeder pigs and mastitis caused by *Escherichia coli* are also important diseases commonly cause by this organism.

Diarrhea in newborn farm animals under 15 days of age is one of the most common diseases which the large animal clinician is faced with in practice. It is a significant cause of economic loss in cattle and swine herds and may assume even greater importance in the future as livestock production becomes more intensified. The effective treatment and control of diarrhea in calves and piglets has been frustrating and usually empirical because the precise etiology cannot usually be determined quickly enough.

For many years following the early work of Smith and Little in which they indicated that *E. coli* was the causative agent of calf diarrhea, it has been accepted that this was the primary pathogen in diarrhea calves and the term colibacillosis has been in common use. Although the existence of colibacillosis in calves, piglets and lambs is still recognized as a disease, diarrhea in newborn calves, for example, can be caused by many different enteropathogens influenced by several epidemiological factors. Thus, colibacillosis is presented in its usual section and the viral diarrheas of newborn farm animals has been expanded in the light of new information.

Many interrelated epidemiological factors have been associated with a high incidence of calf diarrhea and have added to the difficulty of understanding the complexity of the disease. The effects of nutrition of the pregnant dam on the quantity and quality of colostrum and the vigor of the calf are thought to be important but there is little supporting evidence. Changes in weather and wet, windy and cold weather are thought to precipitate outbreaks of the disease in beef calves raised outdoors (3). Increases in population density in calf houses, and on calving grounds, resulting in a high infection rate may in part explain the high incidence in large intensified operations. Some studies have shown that the major contributing factor to dairy calf mortality is the care provided by the calf attendant. Not infrequently, however, outbreaks can occur in herds in which the management is excellent and not uncommonly an etiological diagnosis cannot be made.

Moreover, Salmonellosis is a disease of all animal species caused by a number of different species of salmonellae and manifested clinically by one of three major syndromes; a peracute septicemia, an acute enteritis or a chronic enteritis.

Except in the newborn, especially foals, infection with a *salmonella* is usually not a single cause of the disease salmonellosis. The response to infection with a *Salmonella* sp. varies depending on the size of the challenge dose, the immunological status of the animal, itself dependent on colostrum intake in neonates, previous exposure to infection and expose to stress in older animals. It is generally accepted that the intervention of some precipitating factor such as transport, intercurrent disease, anesthesia and surgery, dosing with antibiotics or anthelmintics, acute deprivation of food, or parturition is usually necessary to cause the disease, salmonellosis, as distinct from infection with *Salmonella* spp.

Many species of salmonellae are capable of causing salmonellosis in animals. The following list includes only the common ones:

| | |
|---|---|
| Cattle: | *S. typhimurium, S. dublin, S. newport* |
| Sheep and goats: | *S. typhimurium, S. dublin, S. anatum* |
| Pigs: | *S. typhimurium, S. choleraesuis* |
| Horse: | *S. typhimurium, S. anatum, S. newport, S. enteriditis, S. heidelberg, S. arizona, S. angona* (75). |

In any discussion about salmonellosis in large animals there is likely to be a significant difference of opinion about its clinical behavior, particularly with respect to the ease with which it spreads and the ease with which it can be controlled. Part of the difference is probably related to the different ways in which animals are managed, particularly the intensity of stocking, and whether or not the animals are housed. But another, and probably greater, part of the difference is because of the different epidemiological characteristics of the *Salmonella* species.

Thus, salmonellosis in cattle is a very serious and continuing disease in areas where it is caused principally by *S. dublin*. But where it is caused by *S. typhimurium* the disease is sporadic and even though it is highly fatal to individual animals it is not really a serious disease.

Although there are probably similar differences with the other species they are not particularly well defined. The difference between the diseases caused by *S. dublin* and *S. typhimurium* is the marked tendency for *S. dublin* to persist in cattle and create a significant reservoir of carrier animals. *S. typhimurium* does not do so as much, so that the disease is likely to subside after an initial exposure, and to recur only when the source of infection, from rodents or feedstuffs, or sewage or slurry, reappears. This does not, of course, preclude the disease from persisting in a flock or herd for long periods.

Because there are so many different strains of *E. coli*, microbiologists classify it into more than 170 serogroups. Within each serogroup there are one or more serotypes. For example, 0126; H and 0126: H27 represent two serotypes of E. coli, with the 0126 signifying the particular serogroup to which these serotypes belong. E. coli 0157: H7 was identified for the first time at the U.S. Centers of Disease Control in 1975. However, it was not until seven years later, in 1982, that E. coli 0157: H7 was conclusively determined to be a cause of enteric disease. Specifically, in 1982, following outbreaks of foodborne illness that involved several cases of bloody diarrhea, E. coli 0157: H7 was firmly associated with hemorrhagic colitis. As a result of this association, E. coli 0157: H7 was designated as an enterohemorrhagic E. colic, or EHEC.

The E. coli 0157: H7 bacterium is believed to mostly live in the intestines of cattle, but has also been found in the intestines of chickens, deer, sheep, and pigs. E. coli 0157: H7 does not make the animals that carry it ill; the animals are merely the reservoir for the bacteria.

Meat typically becomes contaminated with E. coli 0157: H7 during the slaughtering process, when the contents of the animal's intestine are allowed to come into contact with the carcass. Unless the carcass is sanitized somehow, the E. coli bacteria are eventually mixed into the meat, as it is ground into hamburger. Because the bacteria is mixed into the meat during the grinding process, and not just on the surface, thorough cooking is required to prevent E. coli 0157: H7 poisoning when the ground beef is eaten by the consumer.

Contaminated meat looks and smells normal. Although the number of organisms required to cause an infection are not known, it is suspected to be very small.

In U.S. Pat. No. 4,932,400 the instant inventor disclosed a novel method and apparatus for inhibiting shipping fever in livestock which further improved digestibility of consumed feed. In more detail, the Persinger invention provided a unique method comprising the steps of producing a supply of ozone and nitrous oxide gas from ambient air; effecting direct contact between the ozone and nitrous oxide gas and a supply of water by means of a bubbler device to produce a prescribed hydrogen peroxide-nitrous oxide content; continuing such contact to a prescribed range and providing the resultant water supply for use as feed water to the livestock to be treated. Accordingly, by consumption of the unique resultant solution, the treated livestock was found to have increased digestibility of feed. Such treatment was further found to inhibit the growth of pathogenic organisms, thus inhibiting cattle disease such as shipping fever.

The virtues of treating water with ozone gas has long been recognized. For instance, in U.S. Pat. No. 4,176,061, issued to Stopka, there is described an apparatus and method for treatment of fluid with ozone. As recognized by the Stopka patent disclosure, the ability of ozone to purify drinking water has been appreciated for some time. According to Bringmann, the rate of destruction of bacteria by ozone is one to two orders of magnitude faster than chlorine. *Bringmann. G.,* 1954 Determination of The Lethal Activity of Chlorine and Ozone on *E. Coli,* Zhyg. Infektionskar. 139: 130–139.

Among known treatment solutions it is generally recognized that ozone treatment of water will remove several undesirable substances: including pathogens such as fungi, mercpatans and E. coli bacteria, pesticide, etc.

A variety of apparatus is also known for such purposes.

For instance, U.S. Pat. No. 3,726,404 discloses an apparatus for purifying water wherein a batch of water is contained in a tank and fine bubbles of ozone are allowed to rise through the water. Once the batch of water is treated with sufficient amount of ozone, the batch is transferred to a storage tank.

In more detail, one suitable ozone generator means is disclosed in U.S. Pat. No. 4,308,844 issued to James Persinger on Jan. 5, 1982. The disclosure is hereby incorporated by this reference. The apparatus, disclosed in U.S. Pat. No. 4,308,844, comprises an ozone generator cell which acts on ambient air supply. The generator cell produces ozone, oxygen and oxygen ions in the air supply. The generator cell comprises metallic plates and disposed adjacent to one another and separated from each other by a dialectic material and an air gap.

A potential is induced across the adjacent plates and causing ionization of oxygen and nitrogen in the air flowing through the gap which results in the production of ozone gas, nitrous oxide an ionizing air particles.

Accordingly, those skilled in the art have recognized a significant need for a convenient method for reducing bacterial contamination in livestock and other animals. Moreover, there is a need to reduce sources of contamination to other animals such as cattle, sheep, goats, pigs and poultry from feces common in water sources, feed sources, and licking of other animals. The present invention fulfills these needs.

SUMMARY OF THE INVENTION

The present invention relates to an improved method for reducing bacterial contamination and infectious diseases in livestock and other animals, comprising the steps of:
a) producing a gaseous mixture supply of ozone and oxygen gas from ambient air;
b) effecting direct contact between said gaseous mixture derived from step a) with a supply of water for a sufficient time to produce ozone water solution having an effective amount of ozone to remove bacterial substances selected from the group consisting of pathogens, mercpatans, *E. Coli* bacteria, and *Salmonella;*
c) continuing said contact between said gaseous mixture and said water supply until the content of ozone in said water supply is within a range of from about 5 parts per million to about 20 parts per million, and the content of oxygen is between about 80% to about 97% saturation; and
d) providing the resultant solution derived from step c) for use as feed water to the animals to be treated.

Accordingly, the present invention has been found to increase the water intake in treated animals such as steers, swine and chickens, this increases the pH in the digestive system and decreases the volatile fatty acids therein.

Significant improvements were noted in live performance and significant reduction in bacterial contamination.

DESCRIPTION OF THE PREFERRED EMBODIMENTS

Figure 1:
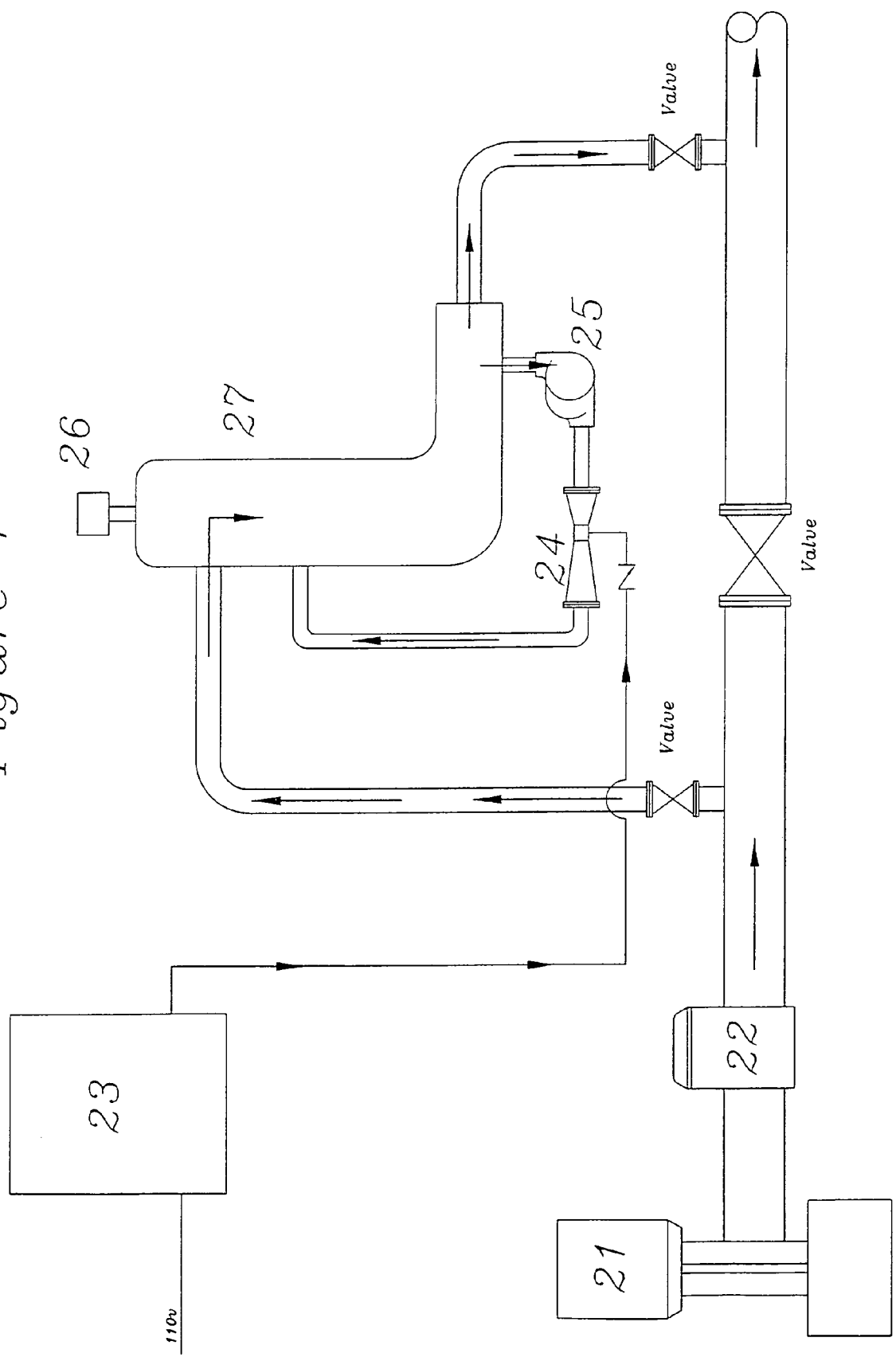
FIG. 1 is a schematic block diagram of one embodied method for treatment of feed water for livestock and other animals comprising prescribed amounts of ionized air, ozone and oxygen gases in accordance with the present invention.

The present invention relates to an improved method for reducing bacterial contamination and infectious diseases in livestock and other animals, comprising the steps of:
a) producing a gaseous mixture supply of ozone and oxygen gas from ambient air;

b) effecting direct contact between said gaseous mixture derived from step a) with a supply of water for a sufficient time to produce ozone water solution having an effective amount of ozone to remove bacterial substances selected from the group consisting of pathogens, mercpatans, *E. Coli* bacteria, and *Salmonella;* c) continuing said contact between said gaseous mixture and said water supply until the content of ozone in said water supply is within a range of from about 5 parts per million to about 20 parts per million, and the content of oxygen is between about 80% to about 97% saturation; and d) providing the resultant solution derived from step c) for use as feed water to the animals to be treated.

Referring now to the drawing, FIG. 1 is a schematic block diagram of one embodied apparatus for producing the inventive drinking water solution comprising prescribed amounts of ionized air, ozone and oxygen gasses and solution in accordance with the present invention. In more detail, shown in FIG. 1 an ionization unit 23 produces the aforementioned gasses and is feed through to a mazzei aspirator 24 into the contact chamber 27. The contact chamber 27 is provided with an air relief valve 26 to vent to the atmosphere. A water well pump 21 delivers water to a storage pressure tank 22. Direct contact of the gaseous mixture of ionized air derived from the ionization unit 23 is admixed in the direct contact chamber with the feed water provided from the storage pressure tank 22. A recirculation pump 25 continuously recirculates the derived solution with a continuous feed of gaseous mixture to bring the resultant solution to the prescribed content of ozone, and oxygen.

Means of producing ozone and oxygen from ambient air—The corona discharge unit manufactured by Oxion, Inc. produces 1,000 to 2,000 ppm ozone and gives the rest of the oxygen a negative charge. The negative charge makes the oxygen several times (5) more soluble in water than ambient air. We use a multipass system with the contact chamber to achieve higher concentrations.

Contamination in water, feed and fecal from other animals. Reduce salmonella in poultry. 10 to 50%–12.5% to 28.7% in example. The higher pH and lower volatile fatty acids will reduce the problems. The animals drink more water. This extra water dilutes the fluids in the digestive tract. This increases the pH and lowers the vfa.

Mode of action as shown in illustrations:

The treated water has a high pH plus they drink more water—this increases pH and lower vfa shown by rumin samples as well as in fecal samples. The animals don't have to be killed to do these samples.

Beef Drinking Water Trial

|  | Untreated | Treated | Change |
| --- | --- | --- | --- |
| Average daily gain, lb/hd/day | 3.31 | 3.53 | +6.64% |
| Feed/Gain 10 pens × 10 pens Dr. Lee | 7.60 | 7.17 | −6.66% |

The bottom line is low pH and high vfa allows the bacteria to live and pass into fecal matter. High pH and lower vfa in digestive system (rumen or stomach) reduces the bacteria that survives and passes into fecal material.

Among known treatment solutions it is generally recognized that ozone treatment of water will remove several undesirable substances: including pathogens such as fungi, mercpatans and *E. coli* bacteria, pesticide, etc.

A variety of apparatus is also known for such purposes.

For instance, U.S. Pat. No. 3,726,404, incorporated by this reference, discloses an apparatus for purifying water wherein a batch of water is contained in a tank and fine bubbles of ozone are allowed to rise through the water. Once the batch of water is treated with sufficient amount of ozone, the batch is transferred to a storage tank.

In more detail, one suitable ozone generator means is disclosed in U.S. Pat. No. 4,308,844 issued to James Persinger on Jan. 5, 1982. The apparatus, disclosed in U.S. Pat. No. 4,308,844, comprises an ozone generator cell which acts on ambient air supply. The generator cell produces ozone, oxygen and oxygen ions in the air supply. The generator cell comprises metallic plates and disposed adjacent to one another and separated from each other by a dialectic material and an air gap.

A potential is induced across the adjacent plates and causing ionization of oxygen and nitrogen in the air flowing through the gap which results in the production of ozone gas, nitrous oxide an ionizing air particles.

In accordance with the present invention, the generator cell produces ozone, oxygen and oxygen ions within the air supply and induces a charge of the mixture by applying an alternating potential of 15,000 volts across the plates. The potential across gap, alternating at a frequency in a range from about 60 to 400 cycles per second, produces ozone gas, nitrous oxide and adds a charge to the air supply.

As described above, the present invention may comprise multiple generator cells, preferably twelve, sequentially connected to produce the desired amount of ionized oxygen.

One suitable ignition transformer for use with the ozone cell is available from Dongan Electric Manufacturing Company of Detroit, Mich. The specifications for the preferred ignition transformer is from about 5,000 volts to about 15,000 volts preferably, has 15,000 volts production at 60 cycle.

If the ambient air is excessively wet, or contained polluting particulates, an air dryer and/or air filter may be used to remove excessive components prior to being fed into a compressor or air mover which flows the supply of air to the ozone generator cell.

Typically, the air supplied to the generator cells should have a minimum flow rate of about 0.4 cubic feet per minute per ozone generator cell. One suitable compressor for this purpose is commercially available from Gast Manufacturing of Bent Harbor, Mich.

After exiting the ozone generator, the supply of the ozone-nitrous oxide gas is directed to a water tank bubbler for effecting direct contact with a supply of water. One suitable water tank bubbler is commercially available from Porex Technology of Fairbourne, Ga. Preferably, the bubbler will produce a relatively small bubble of ozone nitrous oxide mixture for effecting the direct contact, and twenty to about forty microns is preferred for the bubblers specifications.

Any suitable containment means such as a water tank can be used for containment in effecting the prescribed contact between the ozone-nitrous oxide gas supply and water supply to produce the resultant water mixture having about 1,000 parts per million to about 40,000 per million of hydrogen peroxide-nitrous oxide.

Accordingly, the present invention provides an improved method for treatment of feed water for livestock and other animals to reduce bacterial contamination while at the same time improving live performance.

ILLUSTRATIVE EXAMPLE

The inventive method is illustrated by the following representative treatment of a livestock and other animals through the inventive drinking water solution.

The identified animals were grown in finishing areas such as barns or pens with the normal practices accepted by meat producers, except that about one half of the animal population received water that was treated in accordance with the present invention.

Significant improvements were noted in live performance and significant reduction in bacterial contamination.

ILLUSTRATIVE EXAMPLES

|  | Untreated | Treated | Change |
|---|---|---|---|
| 1. Six Ruminally Cannulated Steers  2 Untreated - 4 Treated With Prescribed Solution ||||
| Water pH | 6.26 | 7.55 | +20.6% |
| Water oxygen saturation % | 0.84 | 5.06 | +597.0% |
| Water intake, Liters/d | 8.70 | 24.60 | +182.7% |
| Ruminal pH | 6.10 | 6.44 | +5.6% |
| Ruminal Total VFA, mM | 112.60 | 88.10 | −21.2% |
| 2. Beef Drinking Water Trial ||||
| Average daily gain, lb/hd/day | 3.31 | 3.53 | +6.64% |
| Feed/Gain | 7.60 | 7.17 | −6.66% |
| 10 pens × 10 pens Dr. Lee  3. Swine Drinking Water Trial  Fecal Report ||||
| pH | 7.34 | 7.44 | +1.4% |
| Volatile Fatty Acids, mg/L | 6268.00 | 3780.00 | −40.0% |
| Total colliforms/ml | 1116.00 | 639.00 | −42.7% |
| 4. Drinking Water Trial for Broilers  24 Untreated and 24 Treated Birds Orally Gavaged  With *Salmonella* ||||
| Number of *salmonella* positive | 95.833% | 83.33% | −12.5% |
| Number of *salmonella* per ml carcass rinse solution | 5.02 | 3.58 | −28.7% |

Accordingly, the present invention provides an improved method for treatment of feed water for livestock and other animals to reduce bacterial contamination while at the same time improving live performance.

The invention fulfills the significant need for reducing bacterial contamination in livestock and other animals. Moreover, there is a need to reduce sources of contamination to other animals such as cattle, sheep, goats, pigs and poultry from feces common in water sources, feed source, and licking of other animals. The present invention fulfills these needs.

I claim:

1. An improved method for reducing bacterial contamination and infectious diseases in livestock and other animals, comprising the steps of:
    a) producing a gaseous mixture supply of ozone and oxygen gas from ambient air;
    b) effecting direct contact between said gaseous mixture derived from step a) with a supply of water for a sufficient time to produce ozone water solution having an effective amount of ozone to remove bacterial substances selected from the group consisting of pathogens, mercpatans, *E. Coli* bacteria, and *Salmonella*;
    c) continuing said contact between said gaseous mixture and said water supply until the content of ozone in said water supply is within a range of from about 5 parts per million to about 20 parts per million, and the content of oxygen is between about 80% to about 97% saturation, wherein the pH of said resultant water supply is at least 7.4; and
    d) providing the resultant solution derived from step c) for use as feed water to the animals to be treated.

2. An improved method for reducing bacterial contamination and infectious diseases in livestock and other animals as set forth in claim 1, wherein the bacterial substance is a pathogen.

3. An improved method for reducing bacterial contamination and infectious diseases in livestock and other animals as set forth in claim 1, wherein the bacterial substance is a mercaptan.

4. An improved method for reducing bacterial contamination and infectious diseases in livestock and other animals as set forth in claim 1, wherein the bacterial substance is an *E. Coli* bacteria.

5. An improved method for reducing bacterial contamination and infectious diseases in livestock and other animals as set forth in claim 1, wherein the bacterial substance is *Salmonella*.

* * * * *